(12) United States Patent
Geppert et al.

(10) Patent No.: US 6,716,845 B2
(45) Date of Patent: Apr. 6, 2004

(54) BARBITURIC ACID DERIVATIVES

(75) Inventors: Dagmar Geppert, Penzberg (DE); Frank Grams, Neuenburg-Zienken (DE); Hans-Willi Krell, Penzberg (DE); Herbert Leinert, Heppenheim (DE); Ernesto Menta, Cernusco sul Naviglio (IT); Gerd Zimmermann, Linkenheim-Hochstetten (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 46 days.

(21) Appl. No.: 10/082,907

(22) Filed: Feb. 25, 2002

(65) Prior Publication Data
US 2002/0187991 A1 Dec. 12, 2002

(30) Foreign Application Priority Data

Mar. 30, 2001 (EP) ............................. 01107714

(51) Int. Cl.$^7$ .................. A61K 31/515; C07D 239/02; C07D 403/04
(52) U.S. Cl. .............. 514/252.14; 514/270; 544/295; 544/296; 544/300; 544/301
(58) Field of Search .................. 544/295, 296, 544/301, 300; 514/252.14, 270

(56) References Cited

U.S. PATENT DOCUMENTS 4,595,700 A  6/1986  Donald et al. ............. 514/616

FOREIGN PATENT DOCUMENTS

| DE | 195 48 624 | 6/1997 |
| EP | 0 320 118 | 6/1989 |
| EP | 0 497 192 | 8/1992 |
| EP | 0 489 577 | 3/1995 |
| EP | 0 869 947 | 7/1997 |
| EP | 0988 863 | 3/2000 |
| WO | WO 90/05719 | 5/1990 |
| WO | WO 92/09563 | 6/1992 |
| WO | WO 96/15096 | 5/1996 |
| WO | WO 97/20824 | 6/1997 |
| WO | 97/23465 | * 7/1997 |
| WO | 98/58915 | * 12/1998 |
| WO | WO 01 25217 | 4/2001 |

OTHER PUBLICATIONS

Schnierer et al., Biochemical and Biophysical Research Communications, vol. 191, pp. 319–326 (1993).*
Sumners et al. Annual Reports in Medicinal Chemistry, vol. 33, pp. 131–140 (1996).*
Levy, D. E., Ezrin, A. M., Emerging Drugs vol. 2 (1997) pp. 205–230.
Whittaker, M., Brown, P., Curr. Opin. Drug Discovery Dev. vol. 1 (1998) pp. 157–164.

* cited by examiner

*Primary Examiner*—Richard L. Raymond
(74) *Attorney, Agent, or Firm*—George W. Johnston; Patricia S. Rocha-Tramaloni

(57) ABSTRACT

The present invention pertains to derivatives of 5,5-disubstituted pyrimidine-2,4,6,-trianones having the formula:

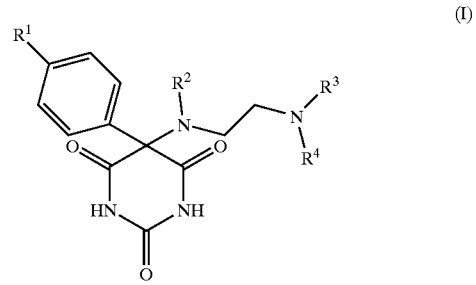

(I)

Figure 1:
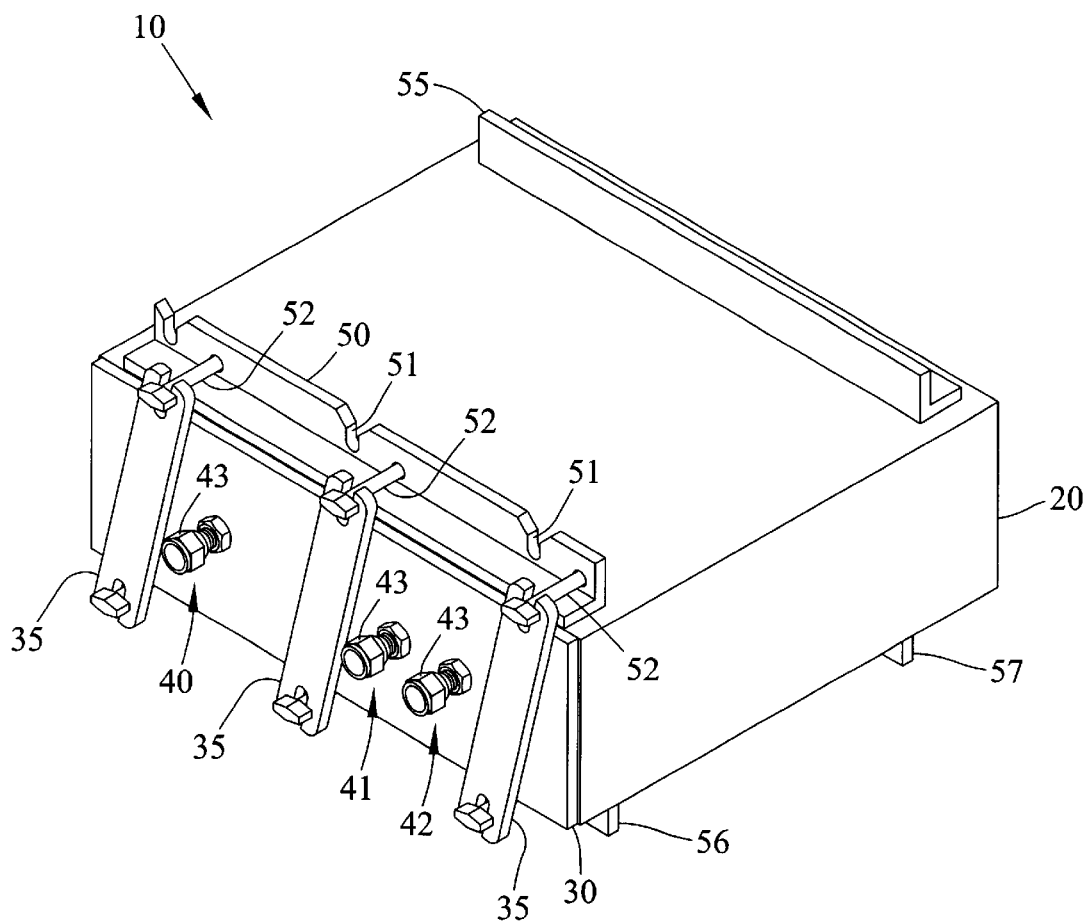

wherein $R^1$, $R^2$, $R^3$, and $R^4$ are described herein. These compounds have antitumor and antimetastatic activity.

9 Claims, 10 Drawing Sheets

BARBITURIC ACID DERIVATIVES

SUMMARY OF THE INVENTION

This invention relates to new derivatives of 5,5-disubstituted pyrimidine-2,4,6-triones of formula I (below). These compounds show a marked antitumor and antimetastatic activity.

BACKGROUND OF THE INVENTION

In normal tissue there is an equilibrium between synthesis and degradation. Extracellular matrix is degraded by proteinases which belong to at least three groups of matrix metalloproteinases. These are the collagenases, gelatinases and stromelysins. Normally there are specific inhibitors for these catabolic enzymes such as $\alpha_2$ macroglobulines and TIMP (=tissue inhibitor of metalloproteinases (MMP)) so that an excessive degradation of extracellular matrix does not occur. Adamalysins are a related group of proteinases. A prominent member of the adamalysins is TACE (TNF-α-converting enzyme).

At least 17 different and yet highly homologous MMP species have been characterized, including the interstitial fibroblast collagenase (MMP-1, HFC), the neutrophil collagenase (MMP-8, HNC), two gelatinases, stromelysins (such as HSL-1) and HPUMP (for a recent review, see Birkedal-Hansen, H., et al., Critical Rev. Oral Biol. Med. 4 (1993) 197–250). These proteinases share a number of structural and functional features but differ somewhat in their substrate specificity. Only HNC and HFC are capable of cleaving type I, II and III native triple-helical collagens at a single bond with the production of fragments ¾ and ¼ of the native chain length. This lowers the collagen melting point and makes them accessible to further attack by other matrix degrading enzymes.

However, the uncontrolled excessive degradation of this matrix is a characteristic of many pathological states such as e.g. in the clinical manifestation of rheumatoid arthritis, osteoarthritis and multiple sclerosis, in the formation of tumor metastases, corneal ulceration, inflammatory diseases and invasion and in diseases of bone and teeth.

The pathogenesis of the foregoing clinical manifestations can be ameliorated by the administration of matrix metalloproteinase inhibitors. A number of such compounds are known (see e.g. the review article of Levy, D. E., Ezrin, A. M., Emerging Drugs 2 (1997) 205–230; Whittaker, M., Brown, P., Curr. Opin. Drug Discovery Dev. 1 (1998) 157–164) or are described in the patent literature, mainly with a hydroxamic acid residue, a thiol or phosphine group as a zinc binding group (see e.g. WO 92/09563 by Glycomed, EP-A 0 497 192 by Hoffmann-La Roche, WO 90/05719 by British Biotechnology, EP-A 0 489 577 by Celltech, EP-A 0 320 118 by Beecham, U.S. Pat. No. 4,595,700 by Searle, WO 97/20824 by Agouron Pharmaceuticals, WO 96/15096 by Bayer Corporation, among others).

Some of these compounds show a high activity as inhibitors of matrix metalloproteinases but their oral availability is very low. Also such compounds often show broad spectrum inhibition of metalloproteinases which may be associated to undesired side-effects and toxicity.

Pyrimidine-2,4,6-trione derivatives have been described in EP 0 869 947 (WO 97/23465) as inhibitors of matrix metalloproteinases. However, there is still a need for new compounds having reduced toxicity and side-effects and a marked inhibitory activity against metalloproteinases, especially as candidates for a chronic treatment against tumor growth and metastasis.

It has now been found that the new pyrimidine-2,4,6-trione derivatives of the present invention have improved activity as matrix metalloproteinase inhibitors as compared to the compounds disclosed in EP 0 869 947.

DETAILED DESCRIPTION OF THE INVENTION

The present invention is directed to compounds of formula I

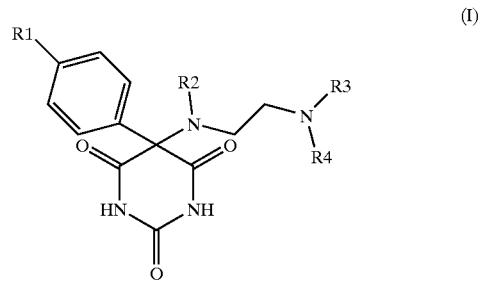

(I)

wherein $R^1$ is selected from the group consisting of a phenyl, phenoxy, phenylthio, phenylsulfinyl, phenylsulfonyl, phenylamino or phenylmethyl residue in which the phenyl moiety optionally may be substituted by one or more halogen atoms, alkoxy, $C_1$–$C_6$ alkyl, cyano, or nitro groups, preferred are substitutions in para and/or meta position by one to two substituents;

$R^2$ is hydrogen;

$R^3$ is selected from the group consisting of hydrogen and lower alkyl, said lower alkyl optionally being interrupted by one or more O, N or S atoms and optionally and independently from each other may be substituted by one or more hydroxyl and oxo groups; and $R^4$ is selected from the group consisting of lower alkyl that optionally may be interrupted by one or more O, N or S atoms and independently from each other may be substituted by one or more hydroxyl, oxo, aryl, aralkyl, heteroaryl or acyl groups; or alternatively, $R^2$ and $R^3$ or $R^3$ and $R^4$ together with the nitrogen atom to which they are bound may form a piperazine ring that optionally may be substituted at the second nitrogen atom by an aryl, aralkyl or a heteroaryl group.

The present invention also encompasses pharmaceutically acceptable salts or prodrugs of the compounds of formula I as well as the use of these compounds to produce pharmaceutical compositions.

The aryl group option for $R^4$ and the piperazine ring resulting from the fusion of $R^3$ and $R^4$ consists of a phenyl ring. The heteroaryl group is understood as a cyclic unsaturated ring system consisting of 5 to 7 ring atoms which can be selected from one or more carbon, nitrogen, oxygen or sulfur atoms. Preferred are electron deficient heteroaryl residues such as the nitrogen containing 6-membered rings like pyridines, pyrimidines, pyrazines or 1,3,5-triazines. Most preferred heteroaryl residues are pyrimidinyl or pyrazinyl.

The aryl, alone or as part of an aralkyl group or heteroaryl rings may be substituted by one or more substituents selected from halogen, hydroxy, alkoxy, amino, dialkylamino, cyano, $C_1$–$C_6$ alkyl, $C_2$–$C_6$ alkenyl, $C_2$–$C_6$ alkinyl, lower acyl, $C_1$–$C_6$ alkylthio $C_1$–$C_6$ alkylsulfonyl, $C_1$–$C_6$ alkylaminocarbonyl, aminocarbonyl, $C_1$–$C_6$ alkylamidosulfonyl, amidosulfonyl, nitro, $C_1$–$C_6$ alkoxycarbonyl, and carboxy. Preferred substitutions are in the para and/or meta positions and preferred substituents are selected from one or two of the above listed substituents.

The aralkyl group is preferably benzyl.

Lower alkyl as used in the definition of $R^3$ and $R^4$ or when used in combinations with other residues denotes $C_1$–$C_6$-alkyl. Preferred lower alkyls are methyl, ethyl, propyl, isopropyl or tert.-butyl.

Preferred $R^3$ and $R^4$ groups are independently selected from the lower alkyl groups that are interrupted by O, N or S, most preferably —$CH_2$—$CH_2$—O—$CH_2$—$CH_2$—OH— $CH_2$—CH(OH)—$CH_2$—O—$CH_2$—$CH_3$; 2-oxo-[1,3]dioxolan-4-ylmethyl; —$CH_2$—CH(OH)—$CH_2$OH; —$CH_2$—CH(OH)—$CH_2$—O—$CH_3$ and $CH_2$—$CH_2{}_{OH}$.

Acyl as used in the definition of $R^4$ denotes CO—($C_1$–$C_6$) alkyl; —C(O)—($C_1$–$C_6$)-alkylen-COOH; —CO-aryl; —CO-aralkyl or —CO-heteroaryl.

Aryl and heteroaryl as used in $R^4$ have the same definitions given above.

Halogen means fluorine, chlorine, bromine and iodine, preferably chlorine or bromine.

If compounds of the formula I contain one or several asymmetric carbon atoms, the optically active compounds of the formula I are also a subject matter of the present invention.

Compounds of the formula I can be synthesized by processes known to those skilled in the art. Preferably compounds of formula I are prepared by reacting a compound of formula II

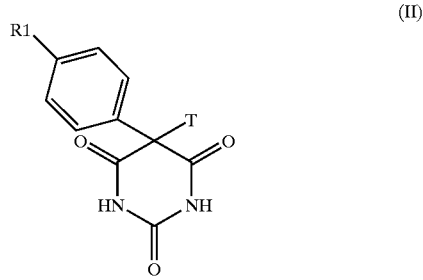

wherein $R^1$ is as defined above and T represents a leaving group such as Hal or $OSO_2R^{10}$, Hal is chlorine, bromine or iodine, and $R^{10}$ is an aryl or a methyl residue, with a compound of formula III

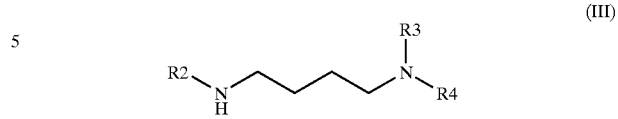

wherein $R^2$, $R^3$ and $R^4$ are as defined above.

Compounds of formula I may then optionally be converted into pharmaceutically acceptable salts by conventional means known to one skilled in the art.

Compounds of the formula II can be synthesized by analogy to known literature procedures. For example pyrimidine-2,4,6-triones brominated in the 5-position can be synthesized by reacting the appropriate bromomalonic acid dialkyl esters with urea (e.g. Acta Chim. Acad. Sci. Hung. 107 (2) (1981) 139). The corresponding brominated or chlorinated compounds of the formula II can be obtained by reacting pyrimidine-2,4,6-triones substituted by R1-Phenyl in the 5-position with bromine (analogous to J. Prakt. Chemie 136 (1933) 329 or J. Chem. Soc. 1931, 1870) or sulfuryl chloride (J. Chem. Soc. 1938, 1622) or N-bromo-succinimide or similar brominating agents. Such procedures are also described in EP 0 869 947.

Amines of the formula III are commercially available, are known in the literature, or can be prepared analogously to published procedures. A preferred procedure for the synthesis of monosubstituted alkylpiperazines consists of alkylating mono-benzyl-piperazine with an alkylating agent such as an alkyl halide, e.g. a bromide or a iodide, or a sulfonate ester of an alcohol, e.g. a tolenesulfonate or methylsulfonate ester, in the presence of a base such as sodium hydride or potassium carbonate in an aprotic solvent like dimethylformamide.

Compounds of formula I wherein $R^4$ is acyl can be prepared by acylation of a compound wherein $R^4$ is hydrogen. Such a compound can be obtained by cleavage of a compound of formula I wherein $R^4$ is a nitrogen protecting group, e.g. benzyl.

Pyrimidine-2,4,6-triones of formula II with T representing hydrogen can be prepared according to known methods by reacting malonic acid esters with urea. See for example J. Med. Chem. 10 (1967) 1078; Helvetica Chem. Acta 34 (1959) 459; Pharmacie 38 (1) (1983) 65, or EP 0 869 947. The reactions are usually carried out in alcohols such as methanol, ethanol or butanol in the presence of an appropriate sodium alcoholate at temperatures between 40° C. and 100° C.

The malonic acid esters which are needed for the preparation of pyrimidine-2,4,6-triones are known from the literature or can be produced according to processes known from the literature. A convenient process for the preparation of malonic acids where $R^1$ has the above mentioned meaning is described in the following scheme:

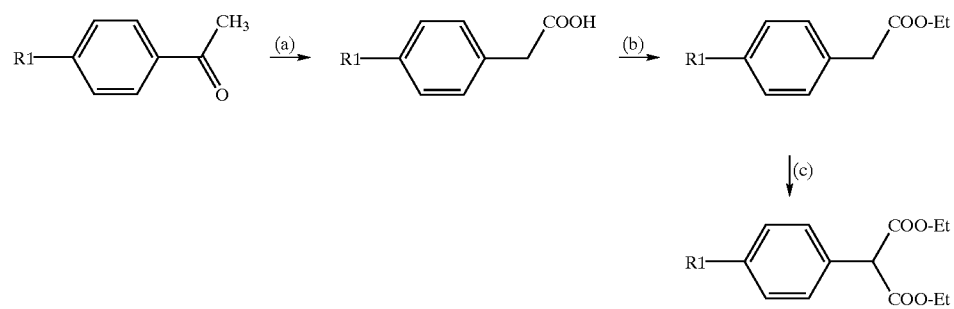

(a) Willgerodt-Kindler reaction
   1. sulfur, morpholine
   2. H$_2$SO$_4$
(b) esterification
(c) Dimethylcarbonate, NaH Examples for these reactions can be found in Houben-Weyl, Vol. E5/2, J. Org. Chem. 46 (1981) 2999 and Arch. Pharm. 323 (1990) 579.

Compounds of the formula I can contain one or several chiral centers and can then be present in a racemic or in an optically active form. The racemates can be separated according to known methods into the enantiomers. Preferably, diastereomeric salts that can be separated by crystallization are formed from the racemic mixtures by reaction with an optically active acid, such as e.g. D- or L-tartaric acid, mandelic acid, malic acid, lactic acid or camphorsulfonic acid, or with an optically active amine, such as e.g. D- or L-α-phenyl-ethylamine, ephedrine, quinidine or cinchonidine.

Alkaline salts, earth alkaline salts like Ca or Mg salts, ammonium salts, acetates or hydrochlorides are mainly used as pharmaceutically acceptable salts which are produced in the usual manner, e.g. by titrating the compounds with inorganic or organic bases or inorganic acids, such as e.g. sodium hydroxide, potassium hydroxide, aqueous ammonia, C$_1$-C$_4$-alkyl-amines such as e.g. triethylamine or hydrochloric acid. The salts are usually purified by reprecipitation from water/acetone.

The new compounds of formula I and salts thereof according to the invention are useful in the preparation of pharmaceutical compositions that can be administered enterally or parenterally in a liquid or solid form. All typical forms of administration of pharmaceutical compositions are appropriate, such as for example tablets, capsules, coated tablets, syrups, solutions, suspensions, etc. Water which contains additives such as stabilizers, solubilizers and buffers that are usual in injection solutions is preferably used as the injection medium.

Additives such as tartrate and citrate buffer, ethanol, complexing agents (such a ethylenediaminetetra-acetic acid and non-toxic salts thereof), high-molecular polymers (such as liquid polyethylene oxide) may be used to regulate viscosity of pharmaceutical compositions according to the invention. Liquid carrier substances for injection solutions have to be sterile and are preferably dispensed into ampoules. Typical solid carriers useful in the preparation of the pharmaceutical compositions of the invention include starch, lactose, mannitol, methylcellulose, talcum, highly dispersed silicic acids, higher molecular fatty acids (such as stearic acid), gelatins, agar-agar, calcium phosphate, magnesium stearate, animal and vegetable fats, solid high-molecular polymers (such as polyethylene glycols).

Pharmaceutical preparations for oral application may also contain flavorings and sweeteners.

The dosage of the compounds of the invention depends on various factors such as manner of administration, species, age and/or individual state of health. A typical therapeutic amount of a compound of formula I is about 10–1000 mg, preferably 100–500 mg administered daily. This daily amount may be given in one single dose or distributed over several doses.

Prodrugs of the compounds of the invention are these compounds that are converted in vivo to the pharmacological active compound. The most common prodrugs are carboxylic acid esters.

The following examples and references are provided to aid the understanding of the present invention, the true scope of which is set forth in the appended claims. It is understood that modifications can be made in the procedures set forth without departing from the spirit of the invention.

EXAMPLES

Unless otherwise stated, each example below was actually performed.

Example 1

5-[4-(4-Chloro-phenoxy)-phenyl]-5-[4-(2,3-dihydroxy-propyl)-piperazin-1-yl]-pyrimidine-2,4,6-trione A) 1-(4-(4-Chloro-phenoxy)-phenyl-ethanone 4-Fluoro-acetophenone (24.4 g) is dissolved in dimethylformamide (180 ml), 4-Chlorophenol (22.8 g) and potassium carbonate (29.5 g) are added. The mixture is heated with stirring for 7 hrs. under reflux. After cooling the mixture is diluted with water and extracted with methylene chloride. The organic phase is washed with water, dried and evaporated to yield 38 g of a crystalline solid. M.p. 66–68° C.

B) 2-(4-(4-Chloro-phenoxy)-phenyl)-morpholine-4-yl-ethanthione 12.4 g of the product obtained by the above procedure are mixed with sulfur (4 g) and morpholine (8.8 ml). The mixture is heated to 150° C. for 2 hrs, cooled in an ice bath and treated with ethanol (20 ml) for 30 minutes. The precipitated crystals are collected and recrystallized from ethanol to yield 13 g of the title compound. M.p. 104–105° C.

C) (4-(4-Chloro-phenoxy)-phenyl)-acetic acid 10.4 g of the compound prepared in step B are heated together with 50% sulfuric acid (200 ml) to 130° C. for 8 hrs. After cooling to room temperature, the reaction mixture is diluted with water (300 ml) and extracted with ethyl acetate. The organic phase is washed with water and subsequently extracted with 2N sodium carbonate solution. The aqueous phase is acidified with dilute hydrochloric acid, ethyl acetate is added, the organic phase is separated, dried and evaporated to yield 5.1 g of a brownish residue. M.p. 98–100° C.

D) (4-(4-Chloro-phenoxy)-phenyl)-acetic acid methyl ester 5.1 g of the product from step C are dissolved in methanol (50 ml). The solution is cooled to −10° C. and treated with thionyl chloride (3 ml) and subsequently heated under reflux for 1 hour. The reaction mixture is evaporated and the residue dissolved in ether. The ether phase is washed with water, dried and evaporated to yield 5.1 g of a reddish brown oil.

E) 2-(4-(4-Chloro-phenoxy)-phenyl)-malonic acid dimethyl ester

A suspension of sodium hydride (350 mg) in dimethyl carbonate (10 ml) is treated at room temperature with the product obtained in step D. The mixture is heated to 90° C. for 1 hour, cooled and poured into ice water and extracted with methylene chloride. The extract is dried and evaporated to yield 5.7 of the title compound as an oil.

F) 5-(4-(4-Chloro-phenoxy)-phenyl)-pyrimidine,2,4,-6-trione

Sodium (800 mg) is dissolved in ethanol (80 ml). To this solution is added urea (1.65 g) and a solution of the compound obtained above in ethanol (5.5 g). The mixture is heated for 3 hours under reflux, cooled to room temperature, treated with ice water (100 ml) and acidified with dilute hydrochloric acid. The precipitate is collected, washed with water and dried to yield 5 g of the title compound. M.p. 257–258° C.

G) 5-Bromo 5-(4-(4-Chloro-phenoxy)-phenyl)-pyrimidine,2,4,-6-trione

A suspension of the compound obtained in step F (6.3 g), N-bromo-succinimide (4.1 g) and dibenzoylperoxide (100 mg) in carbon tetrachloride (120 ml) is stirred for 3 hours at room temperature. The mixture is evaporated, the residue extracted with ethyl acetate. The organic phase is dried and evaporated to yield 7.5 g of the title compound as a thick oil.

H) 1-(2,2-Dimethyl-[1,3]dioxolan-4-ylmethyl)-piperazine

A solution of 2.6 ml N-benzylpiperazine in dimethylformamide (30 ml) is treated slowly with sodium hydride (510 mg). To this suspension is added toluene-4-sulfonic acid 2,2-dimethyl-[1,3]dioxolan-4-ylmethyl ester (0.8 g) and the mixture stirred overnight. The reaction mixture is evaporated, the residue is trated with water and the product extracted with ethyl acetate. The organic extract is dried and evaporated. The crude product is purified by flash chromatography on silica gel using heptane/ethyl acetate 1:1 as eluent. The purified intermediate (0.9 g) is dissolved in methanol (30 ml) and hydrogenated over palladium on charcoal (0.3 g). The catalyst is filtered off and the filtrate is evaporated to yield 0.54 g of the title compound as a waxy solid.

I) 5-(4-(4-Chloro-phenoxy)-phenyl)-5-(4-pyrimidine-2-yl-piperazine)-pyrimidine-2,4,6-trione The product of step G (410 mg) is dissolved in 8 ml of methanol and treated with the product of step H (200 mg). The mixture is stirred overnight. The solvent was evaporated and the residue purified by chromatography on silica gel using methylenechloride/methanol 20:1 as eluent to yield 240 mg of the intermediate product. This product was dissolved in ethanol (10 ml) and treated with HCl in dioxane (10 drops). The mixture was stirred overnight and the solvent evaporated. The residue was triturated with ethylacetate and the solid isolated to yield 200 mg of the title compound which was identified by mass spectrometry using atmospheric pressure ionization (APCI). Found M−H= 486.9, M+H=488.9.

Example 2

The following compounds were prepared using the procedures of example 1 replacing 4-chlorophenol by the corresponding phenols and the dihydroxyethyl-piperazine by the corresponding piperazines. The final products were identified by mass spectrometry using atmospheric pressure ionization (APCI).

| Compound Number | Chemical name | mass spectra (APCI) |
|---|---|---|
| 1 | 5-[4-4-Chloro-phenoxy)-phenyl]-5-4-[2-2-hydroxy-ethoxy)-ethyl]-piperazin-1-yl-pyrimidine-2,4,6-trione | [M + H] 502.9 calc. 503.17 |
| 2 | 5-[4-(4-Chloro-phenoxy)-phenyl]-5-[4-(2-oxo-[1,3]dioxolan-4-ylmethyl)-piperazin-1-yl]-pyrimidine-2,4,6-trione | [M + H] 514.8 calc. 515.14 |
| 3 | 5-[4-(4-Chloro-phenoxy)-phenyl]-5-[4-(3-ethoxy-2-hydroxy-propyl)-piperazin-1-yl]-pyrimidine-2,4,6-trione | [M + H] 517.0 calc. 517.19 |
| 4 | 5-[4-(3,4-Dichloro-phenoxy)-phenyl]-5-4-[2-(2-hydroxy-ethoxy)-ethyl]-piperazin-1-yl-pyrimidine-2,4,6-trione | [M + H] 537 calc. 537.13 |
| 5 | 5-4-[2-(2-Hydroxy-ethoxy)-ethyl]-piperazin-1-yl-5-(4-phenylsulfanyl-phenyl)-pyrimidine-2,4,6-trione | [M + H] 484.9 calc. 485.19 |
| 6 | 5-[4-(4-Chloro-phenoxy)-phenyl]-5-[4-(2-hydroxy-3-methoxy-propyl)-piperazin-1-yl]-pyrimidine-2,4,6-trione | [M + H] 502.9 calc. 503.17 |
| 7 | 5-4-[2-(2-Hydroxy-ethoxy)-ethyl]-piperazin-1-yl-5-(4-phenoxy-phenyl)-pyrimidine-2,4,6-trione | [M + H] 469 calc. 469.21 |
| 8 | 5-[4-(3-Ethoxy-2-hydroxy-propyl)-piperazin-1-yl]-5-(4-phenoxy-phenyl)-pyrimidine-2,4,6-trione | [M + H] 483.0 calc. 483.23 |
| 9 | 5-2-[Bis-(2-hydroxy-ethyl)-amino]-ethylamino-5-[4-(4-bromo-phenoxy)-phenyl]-pyrimidine-2,4,6-trione* | [M + H] 519.8 calc. 521.11 |
| 10 | 5-[4-(4-Bromo-phenoxy)-phenyl]-5-[2-(4-pyrimidin-2-yl-piperazin-1-yl)-ethylamino]-pyrimidine-2,4,6-trione | [M + H] 579.8 calc. 580.13 |
| 11 | 4-(4-5-[4-(4-Bromo-phenoxy)-phenyl]-2,4,6-trioxo-hexahydro-pyrimidin-5-yl-piperazin-1-ylmethyl)-benzenesulfonamide | [M + H] 627.7 calc. 628.09 |

*isolated as hydrochloride

Example 3

4-Oxo-4-4-[2,4,6-trioxo-5-(4-phenoxy-phenyl)-hexahydro-pyrimidin-5-yl]-piperazin-1-yl-butyric acid 5-Bromo-5-(4-(phenoxy)-phenyl)-pyrimidine,2,4,-6-trione prepared analogously to Example 2 procedure H and N-benzyl-piperazine are reacted according to procedure I of Example 1. The product is hydrogenated over palladium on charcoal to yield the very insoluble 5-piperazino-5-(4-(phenoxy)-phenyl)-pyrimidine,2,4,-6-trione (m.p. 270–275 C.). This compound (190 mg) was dissolved in dimethylformamide (10 ml) and treated with succinic anhydride (60 mg) in the presence of p-dimethylamino-pyridine (6 mg) as catalyst. The mixture was further diluted with tetrahydrofurane and kept for 48 hours at room temperature. The crude material obtained after evaporation of the solvent was purified by chromatography on silica gel using dichloromethane/methanol 9:1 as eluent. Pooling the product containing fractions yielded 95 mg of the title compound identified by mass spectrometry using atmospheric pressure ionization. [M+H]=480.9, [M+Na]=503.

Example 4

In order to determine the inhibition of MMPs, for example HNC (MMP-8), the catalytic domain (isolation and purification see for example Schnierer, S., et al., Biochem. Biophys. Res. Commun. 191 (1993) 319–326) is incubated with inhibitors having various concentrations. Subsequently, the initial reaction rate in the conversion of a standard substrate is measured in a manner analogous to Grams, F., et al., FEBS 335 (1993) 76–80.

The results are evaluated by plotting the reciprocal reaction rate against the concentration of the inhibitor. The inhibition constant (Ki) is obtained as the negative section of the abscissis by the graphical method according to Dixon, M., Biochem. J. 55 (1953) 170–202.

The synthetic collagenase substrate is a heptapeptide which is coupled, at the C terminus, with DNP (dinitrophenol). Said DNP residue quenches by steric hindrance the fluorescence of the adjacent tryptophane of the heptapeptide. After cleavage of a tripeptide which includes the DNP group, the tryptophane fluorescence increases. The proteolytic cleavage of the substrate therefore can be measured by the fluorescence value.

a) First method

The assay was performed at 25° C. in a freshly prepared 50 mM Tris buffer (pH 8.0) treated with dithiozone to remove traces of heavy metals. 4 mM $CaCl_2$ was added and the buffer saturated with argon. Stock solutions of adamalysin II were prepared by centrifugation of the protein from an ammonium sulfate suspension and subsequent dissolution in the assay buffer. Stock solutions of collagenase were diluted with the assay buffer. Enzyme concentrations were determined by uv measurements ($\epsilon_{280}$=2.8 $10^4$ $M^{-1}$ $cm^{-1}$, $\epsilon_{288}$: 2.2 $10^4$ $M^{-1} \cdot cm^{-1}$) and the stock solutions were stored in the cold. This solution was diluted 1:100 to obtain the final 16 nM assay concentration. The fluorogenic substrate DNP-Pro-Leu-Gly-Leu-Trp-Ala-D-Arg-$NH_2$ with a $K_m$ of 52 $\mu M$ was used at a concentration of 21.4 $\mu M$; for the $K_i$ determination a 12.8 $\mu M$ concentration has also been used. Substrate fluorescence was measured at an excitation and emission wavelength of $\lambda$=320 and 420 nm, respectively, on a spectrofluorimeter (Perkin Elmer, Model 650-40) equipped with a thermostated cell holder. Substrate hydrolysis was monitored for 10 min. immediately after adding the enzyme. All reactions were performed at least in triplicate. The $K_i$ values-of the inhibitors were calculated from the intersection point of the straight lines obtained by the plots of $v_o/v_i$ vs. [concentration of inhibitor], whereas $IC_{50}$ values were calculated from plots of $v_i/v_o$ [concentration of inhibitor] by non-linear regression with simple robust weighting.

b) Second method

Assay Buffer 50 mM Tris/HCI pH 7.6 (Tris=Tris-(hydroxymethyl)-aminomethane)

100 mM NaCl/10 mM CaCl2/5% MeOH (if necessary)

Enzyme: 8 nM catalytic domain (Met80-Gly242) of human neutrophil collagenase (MMP-8)

Substrate: 10 microM DNP-Pro-Leu-Gly-Leu-Trp-Ala-D-Arg-NH2

Total assay volume: 1 ml

A solution of the enzyme and inhibitor in assay buffer (25° C.) was prepared. The reaction was started by giving the substrate into the solution. The cleavage of the fluorogenic substrate was followed by fluorescence spectroscopy with an excitation and emission wavelength of 280 and 350 nm, respectively. The $IC_{50}$ value was calculated as the inhibitor concentration, which is necessary to decrease the velocity of the reaction to the half in comparison to the reaction without inhibitor.

Table 1 shows the $IC_{50}$ values found in comparison with the compounds of example 26 and preferred compound no. 118 from EP 0 869 947.

TABLE 1

$IC_{50}$ Values of MMP-Inhibitor (vs. MMP-8, catalytic domain)

|  | $IC_{50}$ [nM] |
| --- | --- |
| Comparative Compounds from EP 0 869 947 | |
| preferred no. 118 | 60 |
| example 26 | 15 |
| Compounds of the Invention | |
| Example 1 | 11 |
| Example 2 - no. 1 | 16 |
| Example 2 - no. 2 | 9 |
| Example 2 - no. 3 | 15 |
| Example 2 - no. 4 | 7 |
| Example 2 - no. 5 | 19 |
| Example 2 - no. 10 | 9 |
| Example 2 - no. 11 | 11 |
| Example 3 | 11 |

What is claimed is:

1. A compound of formula I

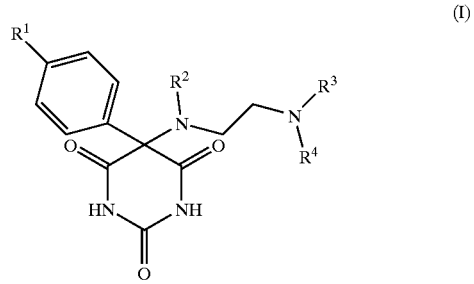

(I)

wherein $R^1$ is selected from the group consisting of a phenyl, phenoxy, phenylthio, phenylsulfinyl, phenylsulfonyl, phenylamino and phenylmethyl residue, in which the phenyl moiety can be substituted by one or more halogen atoms, alkoxy, $C_1$–$C_6$ alkyl, cyano, or nitro groups;

$R^2$ is hydrogen;

$R^3$ is selected from the group consisting of hydrogen and lower alkyl, said lower alkyl group being optionally interrupted by one or more O, N or S atoms and optionally and independently being substituted by one or more substituents selected from the group consisting of hydroxyl and oxo; and $R^4$ is selected from the group consisting of lower alkyl that optionally may be interrupted by one or more O, N or S atoms and optionally and independently being substituted by one or more substituents selected from the group consisting of hydroxyl, oxo, aryl, aralkyl, heteroaryl and acyl; or alternatively $R^2$ and $R^3$ together with the nitrogen atom to which they are bound may form a piperazine ring, provided that in such case $R^4$ is not lower alkyl substituted by one hydroxyl group, or alternatively, $R^3$ and $R^4$ together with the nitrogen atom to which they are bound may form a piperazine ring that may be unsubstituted or substituted at the second nitrogen atom by an aryl, aralkyl or heteroaryl group;

and the pharmaceutically acceptable salts and prodrugs of the compounds of formula I.

2. The compound of claim 1 wherein $R^1$ is unsubstituted phenoxy or phenylthio, or phenoxy substituted by chloro, bromo, methyl or tert.butyl.

3. The compound of claim 1 wherein $R^2$ and $R^3$ form a piperazine ring, and $R^4$ is selected from —CH$_2$—CH$_2$—O—CH$_2$—CH$_2$—OH; —CH$_2$—CH(OH)—CH$_2$—OH; —CH$_2$—CH(OH)—CH$_2$—O—CH$_2$—CH$_3$; —CH$_2$—CH(OH)—CH$_2$—O—CH$_3$; 2-oxo[1,3]dioxolan-4-ylmethyl and 4-sulfonamido-benzyl.

4. The compound of claim 1 wherein $R^3$ and $R^4$ form a piperazine ring that is substituted by pyrimidinyl.

5. The compound of claim 1 wherein $R^3$ and $R^4$ are each —CH$_2$CH$_2$OH.

6. The compound of claim 1 wherein the phenyl moiety is substituted in the para or meta positions, or para and meta positions.

7. A compound selected from the group consisting of

5-[4-(4-Chloro-phenoxy)-phenyl]-5-[4-(2,3-dihydroxy-propyl)-piperazin-1-yl]-pyrimidine-2,4,6-trione;

5-[4-(4-Chloro-phenoxy)-phenyl]-5-4-[2-(2-hydroxy-ethoxy)-ethyl]-piperazin-1-yl-pyrimidine-2,4,6-trione;

5-[4-(4-Chloro-phenoxy)-phenyl]-5-[4-(2-oxo-[1,3]dioxolan-4-ylmethyl)-piperazin-1-yl]-pyrimidine-2,4,6-trione;

5-[4-(4-Chloro-phenoxy)-phenyl]-5-[4-(3-ethoxy-2-hydroxy-propyl)-piperazin-1-yl]-pyrimidine-2,4,6-trione;

5-[4-(3,4-Dichloro-phenoxy)-phenyl]-5-4-[2-(2-hydroxy-ethoxy)-ethyl]-piperazin-1-yl-pyrimidine-2,4,6-trione;

5-4-[2-(2-Hydroxy-ethoxy)-ethyl]-piperazin-1-yl-5-(4-phenylsulfanyl-phenyl)-pyrimidine-2,4,6-trione;

5-[4-(4-Chloro-phenoxy)-phenyl]-5-[4-(2-hydroxy-3-methoxy-propyl)-piperazin-1-yl]-pyrimidine-2,4,6-trione;

5-4-[2-(2-Hydroxy-ethoxy)-ethyl]-piperazin-1-yl-5-(4-phenoxy-phenyl)-pyrimidine-2,4,6-trione;

5-[4-(3-Ethoxy-2-hydroxy-propyl)-piperazin-1-yl]-5-(4-phenoxy-phenyl)-pyrimidine-2,4,6-trione;

5-2-[Bis-(2-hydroxy-ethyl)-amino]-ethylamino-5-[4-(4-bromo-phenoxy)-phenyl]-pyrimidine-2,4,6-trione;

5-[4-(4-Bromo-phenoxy)-phenyl]-5-[2-(4-pyrimidin-2-yl-piperazin-1-yl)-ethylamino]-pyrimidine-2,4,6-trione;

4-(4-5-[4-(4-Bromo-phenoxy)-phenyl]-2,4,6-trioxo-hexahydro-pyrimidin-5-yl-piperazin-1-ylmethyl)-benzenesulfonamide; and 4-Oxo-4-4-[2,4,6-trioxo-5-(4-phenoxy-phenyl)-hexahydro-pyrimidin-5-yl]-piperazin-1-yl-butyric acid.

8. A pharmaceutical composition containing as an active ingredient a therapeutically effective amount of a compound of claim 1 and a pharmaceutically acceptable excipient or diluent.

9. A method of treating a solid tumor comprising administering to a patient in need of such treatment a therapeutically effective amount of a compound of claim 1.

* * * * *

UNITED STATES PATENT AND TRADEMARK OFFICE
CERTIFICATE OF CORRECTION

PATENT NO. : 6,716,845 B2
DATED : April 6, 2004
INVENTOR(S) : Dagmar Geppert et al.

Figure 2:
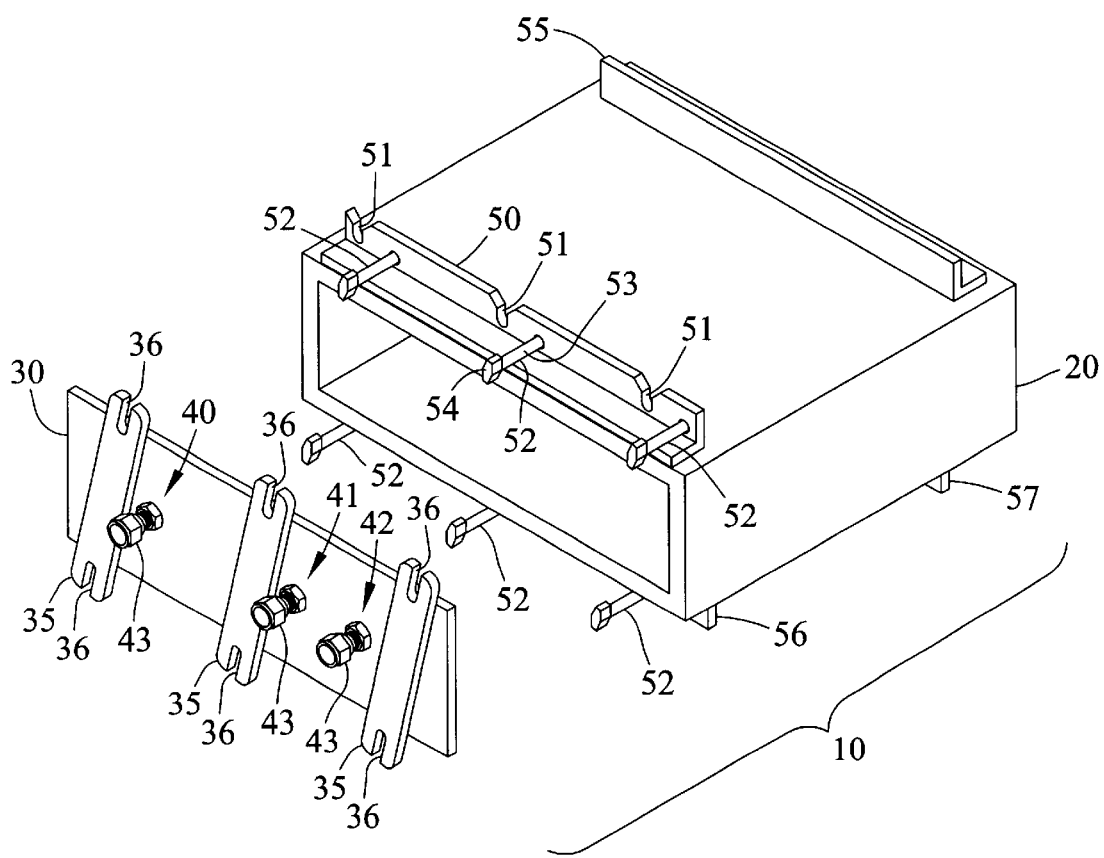
Figure 3:
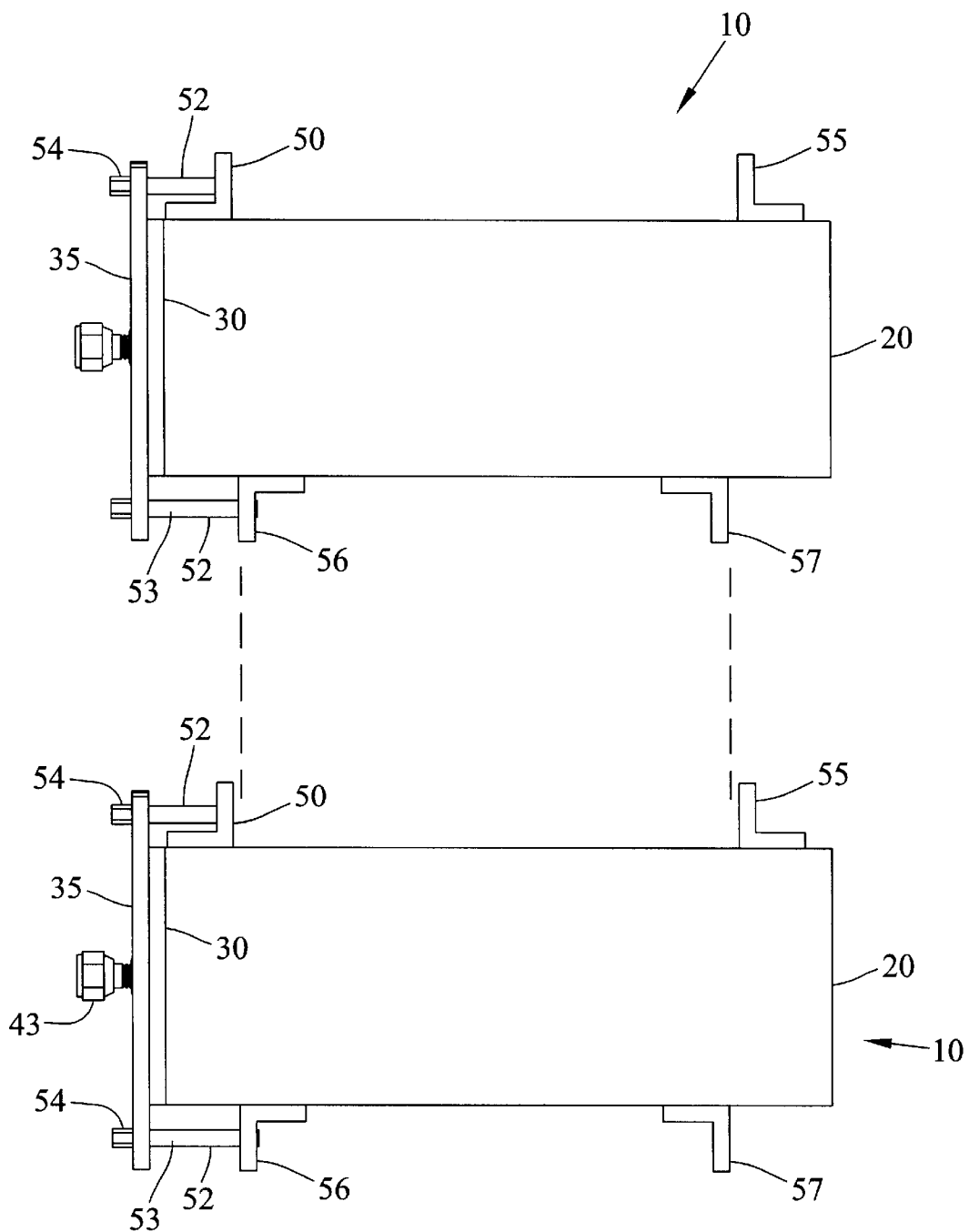
Figure 4:
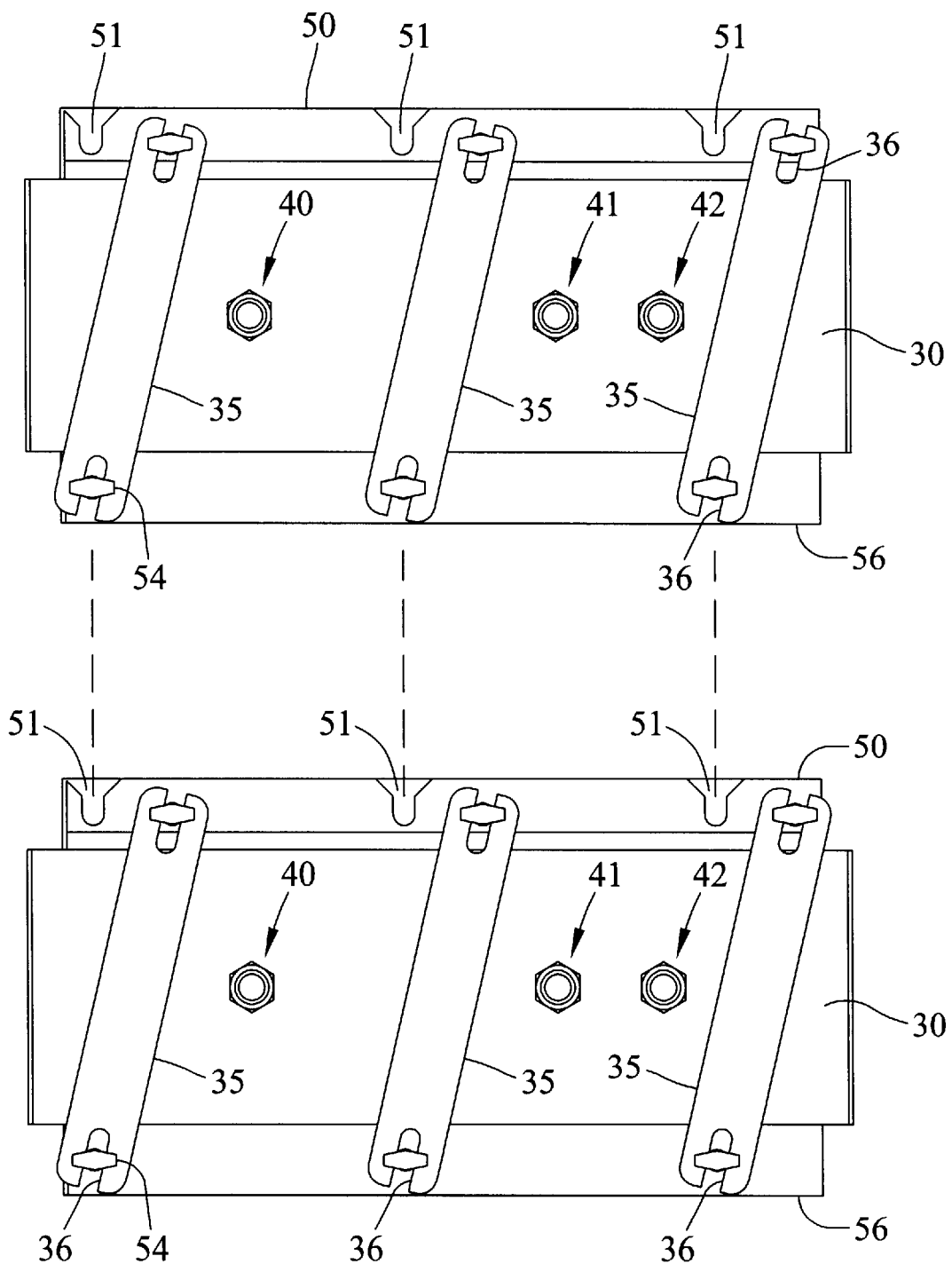
Figure 5:
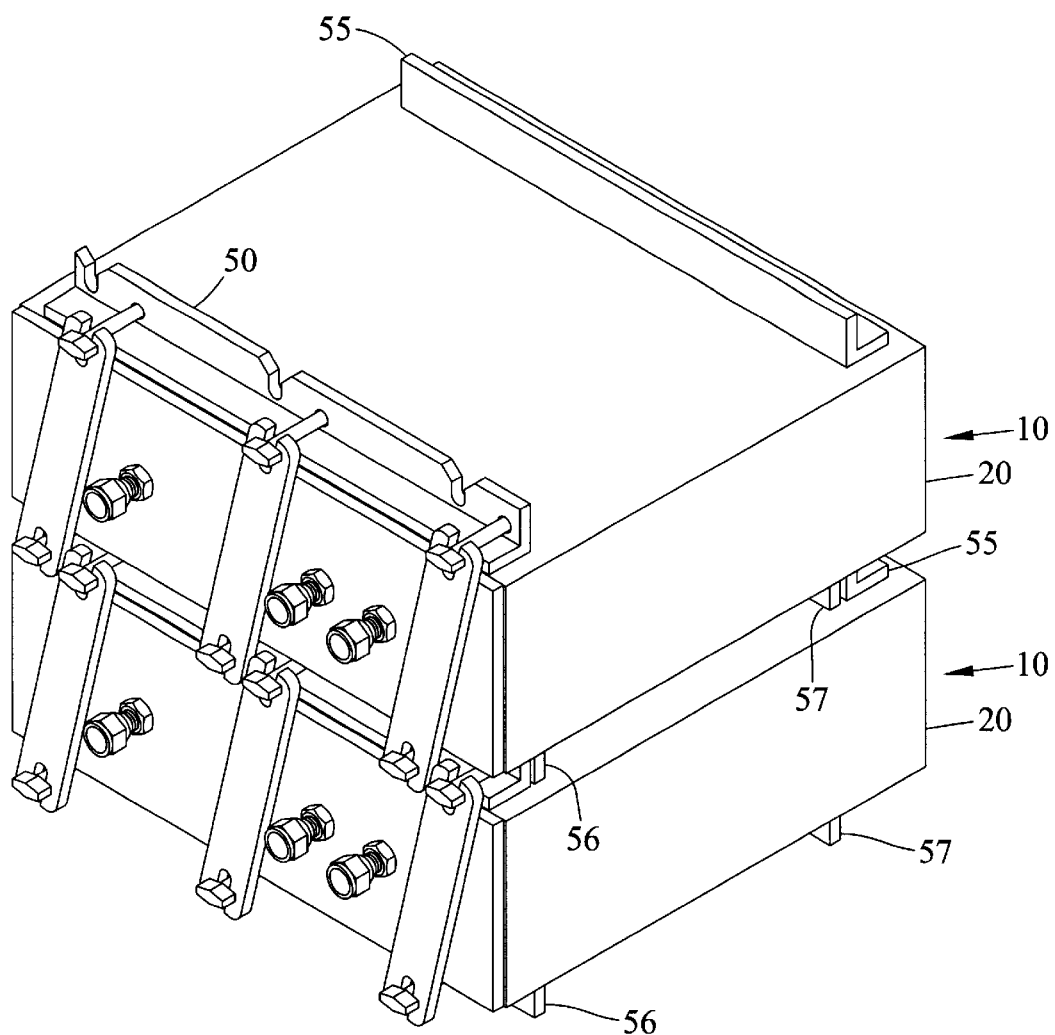
Figure 6:
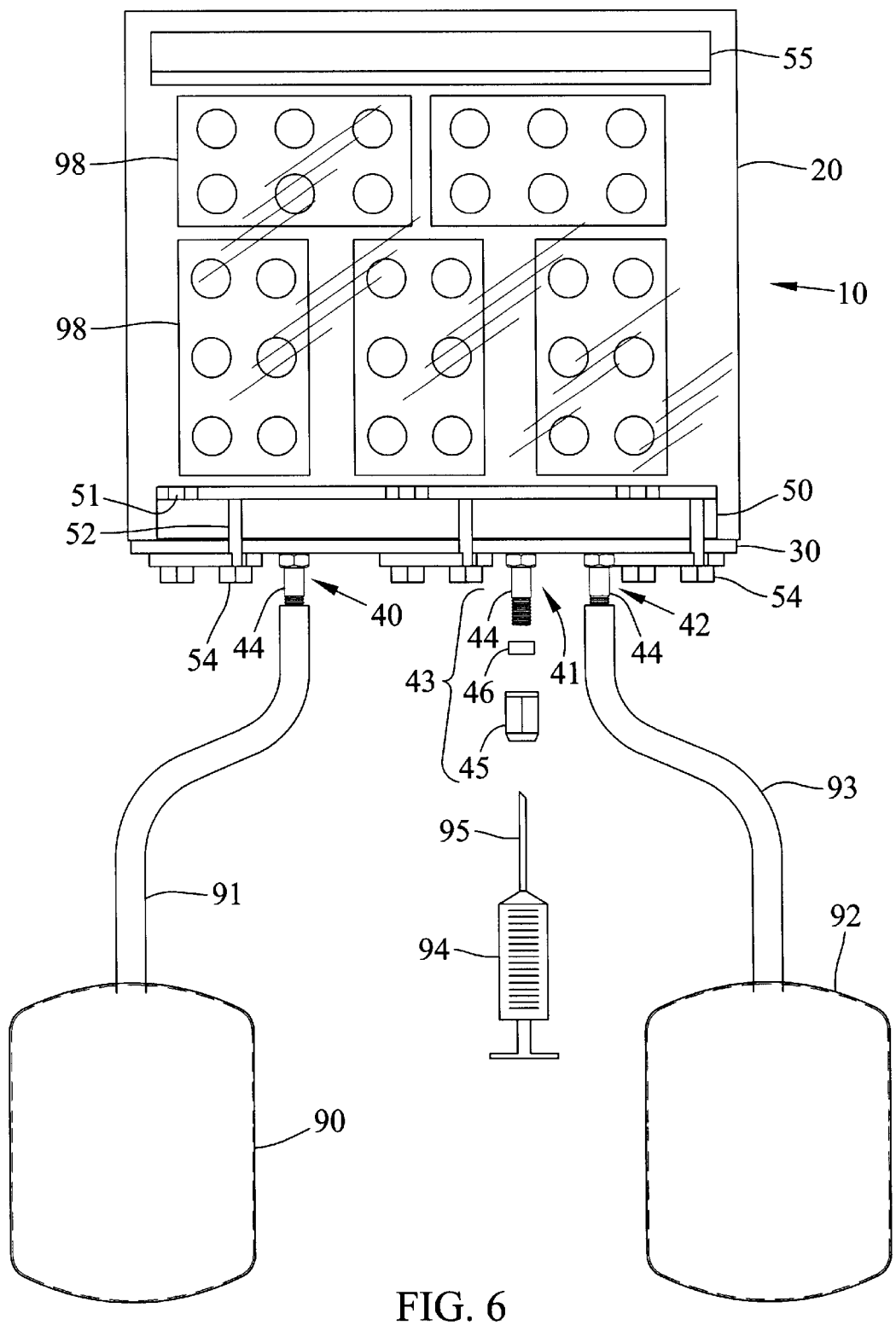
Figure 7:
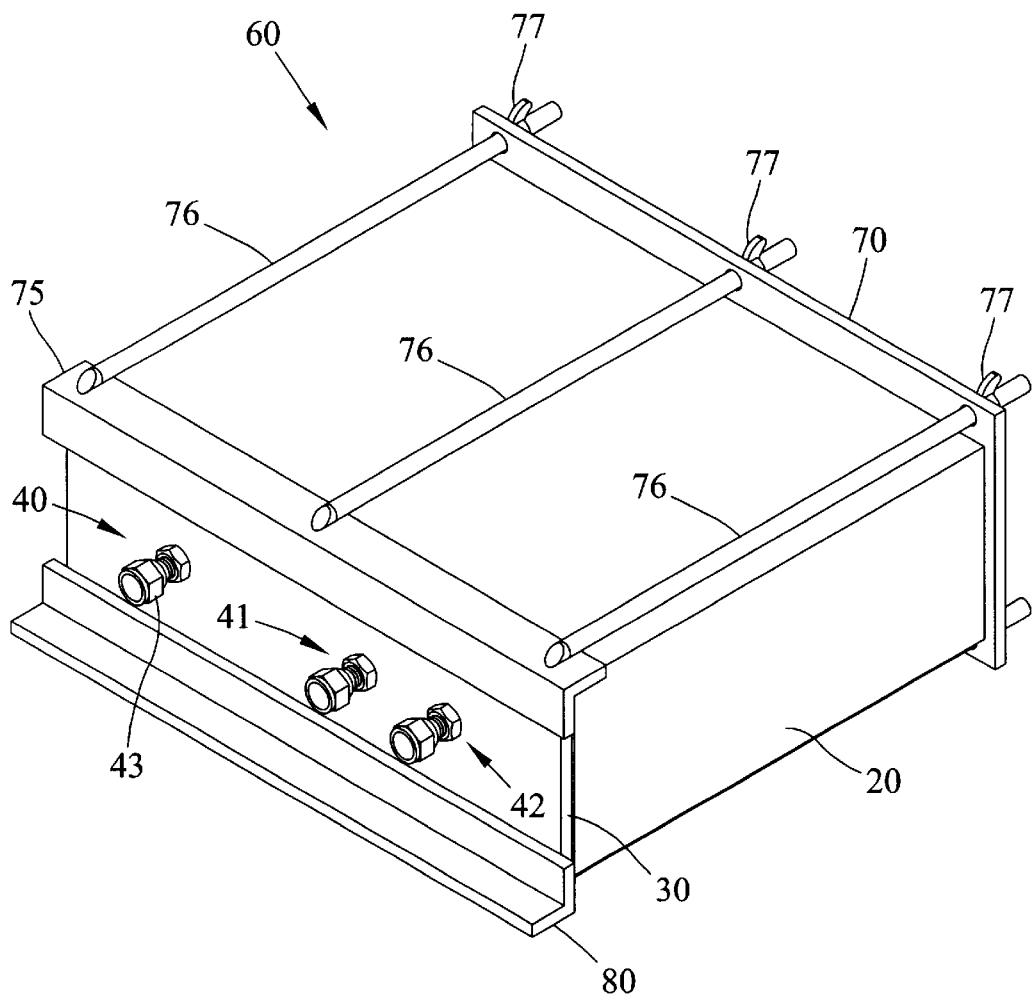
Figure 8:
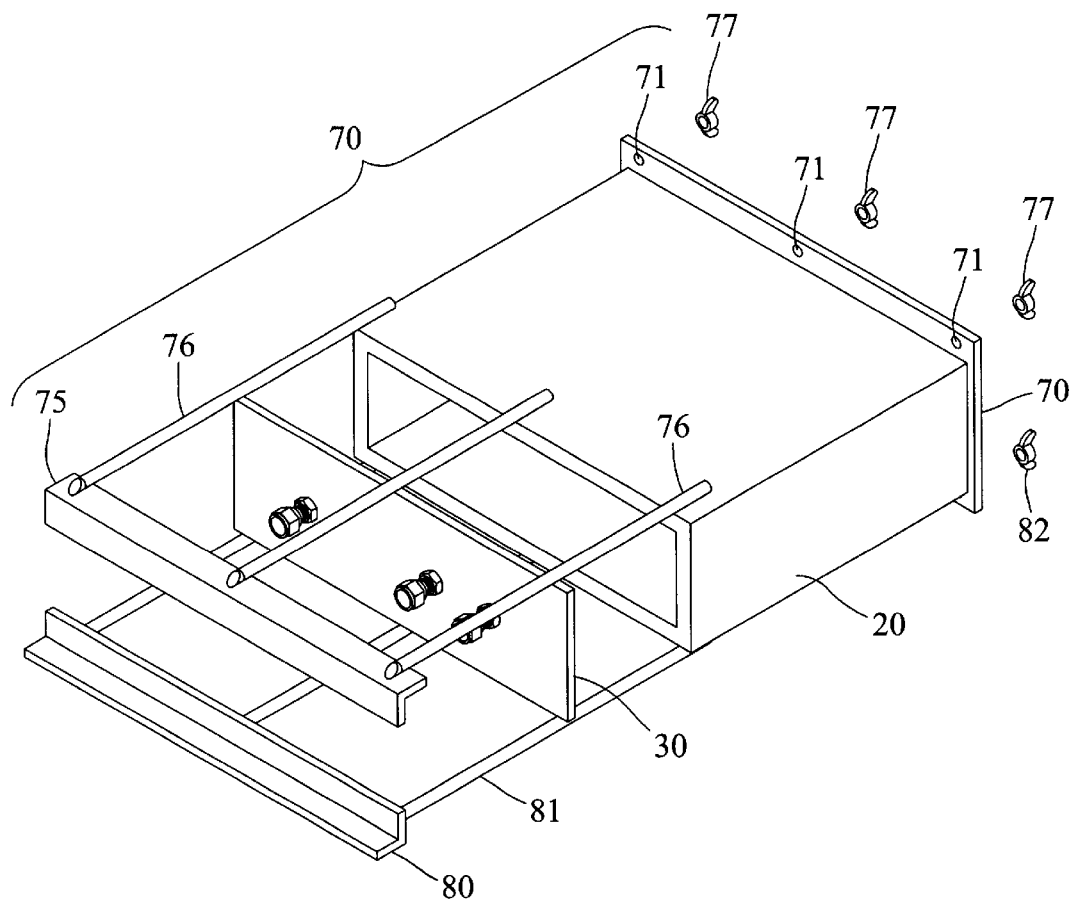
Figure 9:
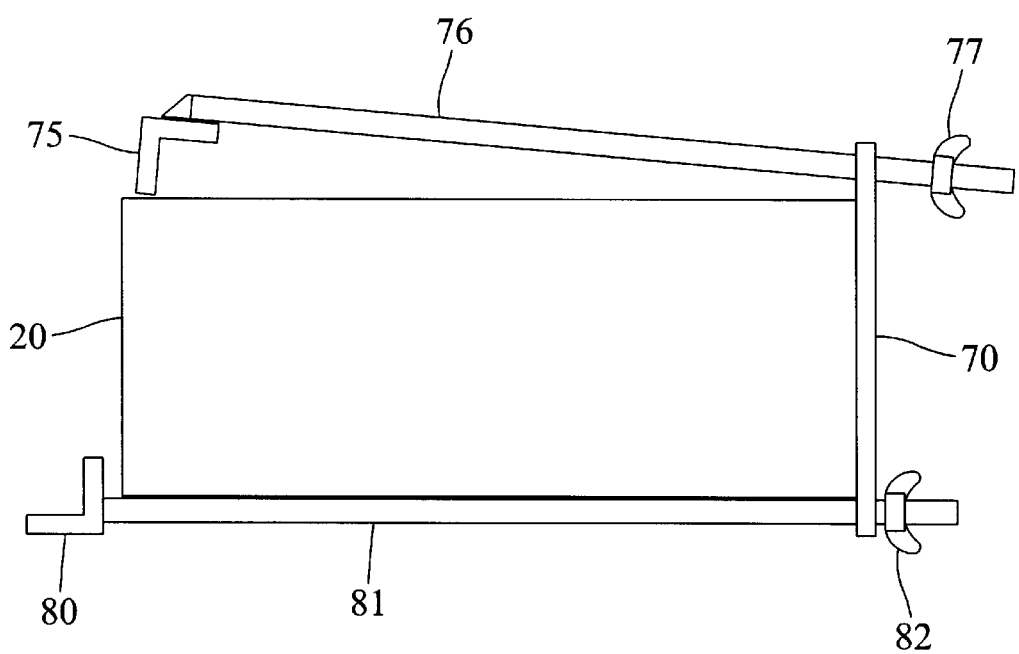
Figure 10:
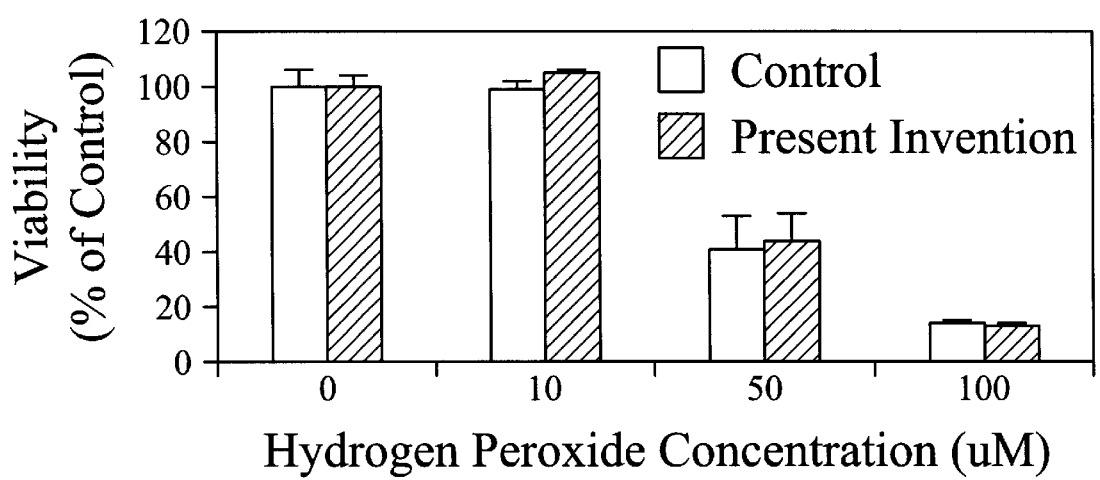

It is certified that error appears in the above-identified patent and that said Letters Patent is hereby corrected as shown below:

<u>Drawings,</u>
Sheets1 to 10 showing Figures 1-10 should be removed.

Signed and Sealed this

Sixth Day of July, 2004

JON W. DUDAS
*Acting Director of the United States Patent and Trademark Office*